US005490848A

United States Patent [19]

Finley et al.

[11] Patent Number: 5,490,848

[45] Date of Patent: Feb. 13, 1996

[54] SYSTEM FOR CREATING ON SITE, REMOTE FROM A STERILE ENVIRONMENT, PARENTERAL SOLUTIONS

[75] Inventors: Mike Finley, Park City; Mike Scharf, McHenry; Jeff Packard, Grayslake; Jim Kipp; Tom Dudar, both of Palatine; Jim Owens, McHenry; Al Bindokas, Clarendon Hills, all of Ill.

[73] Assignee: The United States of America as represented by the Administrator of the National Aeronautics and Space Administration, Washington, D.C.

[21] Appl. No.: 647,113

[22] Filed: Jan. 29, 1991

[51] Int. Cl.[6] .................... A61M 5/00

[52] U.S. Cl. .................... 604/403; 604/408; 604/416

[58] Field of Search .................... 604/403–416, 604/247–253, 29, 85, 86

[56] References Cited

U.S. PATENT DOCUMENTS

| | | | |
|---|---|---|---|
| 3,889,674 | 6/1975 | Cilento . | |
| 3,924,741 | 12/1975 | Kachur et al. . | |
| 3,978,857 | 9/1976 | McPhee | 604/406 |
| 4,031,892 | 6/1977 | Hurshman . | |
| 4,031,895 | 6/1977 | Porter . | |
| 4,059,109 | 11/1977 | Tischlinger . | |
| 4,122,943 | 10/1978 | Silver et al. . | |
| 4,171,698 | 10/1979 | Genese . | |
| 4,172,457 | 10/1979 | Choksi et al. . | |
| 4,177,938 | 12/1979 | Brina . | |
| 4,180,070 | 12/1979 | Genese . | |
| 4,234,083 | 11/1980 | Cohen . | |
| 4,243,080 | 1/1981 | Choksi et al. . | |
| 4,254,768 | 3/1981 | Ty . | |
| 4,259,952 | 4/1981 | Avoy . | |
| 4,265,760 | 5/1981 | Abel et al. . | |
| 4,282,863 | 8/1981 | Biegler et al. | 604/410 |
| 4,296,786 | 10/1981 | Brignola . | |
| 4,315,570 | 2/1982 | Silver et al. . | |
| 4,328,802 | 5/1982 | Curley et al. . | |
| 4,392,850 | 7/1983 | Elias et al. . | |
| 4,392,851 | 7/1983 | Elias . | |
| 4,396,382 | 8/1983 | Goldhaber | 604/28 |
| 4,396,383 | 8/1983 | Hart . | |
| 4,410,321 | 10/1983 | Pearson et al. . | |
| 4,424,057 | 1/1984 | House . | |
| 4,432,755 | 2/1984 | Pearson . | |
| 4,433,974 | 2/1984 | Bischof . | |
| 4,458,733 | 7/1984 | Lyons | 604/410 X |
| 4,465,471 | 8/1984 | Harris et al. . | |
| 4,467,588 | 8/1984 | Carveth | 604/410 X |
| 4,479,578 | 10/1984 | Brignola et al. . | |
| 4,484,920 | 11/1984 | Kaufman et al. . | |
| 4,504,265 | 3/1985 | Rudzena et al. | 604/86 |
| 4,509,861 | 4/1985 | Sjonell . | |
| 4,511,352 | 4/1985 | Theeuwes et al. . | |
| 4,515,586 | 4/1985 | Mendenhall et al. . | |

(List continued on next page.)

FOREIGN PATENT DOCUMENTS

| | | |
|---|---|---|
| 3333283 | 4/1985 | Germany . |

*Primary Examiner*—Sam Rimell
*Attorney, Agent, or Firm*—Mark J. Buonaiuto; Paul C. Flattery; Amy L. H. Rockwell

[57] ABSTRACT

The present invention provides a system and method for creating on site, remote from a sterile environment, parenteral solutions in large volume parenteral containers for intravenous administration to a patient. In an embodiment, this system comprises an empty large volume container including at least one port for accessing an interior of the container. The port includes a sterilizing filter for sterilizing a fluid fed through the port into the container. A second container is provided including a solute and having means for coupling the second container to the large volume container and thereby providing fluid communication therebetween allowing the solute to be received within the interior of the container. A sterile water source is also provided including means for placing the sterile water source in fluid communication with the port and allowing water to flow from the sterile water source into the interior of the container. This allows the solute, and sterile water that has been fed through the filter, to create a parenteral solution in the large volume parenteral container.

47 Claims, 2 Drawing Sheets

FOREIGN PATENT DOCUMENTS

| | | | |
|---|---|---|---|
| 4,548,606 | 5/1985 | Larkin . | |
| 4,573,506 | 3/1986 | Paoletti . | |
| 4,581,016 | 4/1986 | Gettig . | |
| 4,583,971 | 4/1986 | Bocquet et al. . | |
| 4,589,879 | 5/1986 | Pearson . | |
| 4,591,049 | 5/1986 | Walter et al. . | |
| 4,591,357 | 5/1986 | Sneider . | |
| 4,601,704 | 7/1986 | Larkin . | |
| 4,602,910 | 7/1986 | Larkin . | |
| 4,606,734 | 8/1986 | Larkin et al. . | |
| 4,608,043 | 8/1986 | Larkin et al. . | |
| 4,609,369 | 9/1986 | Ball . | |
| 4,610,374 | 9/1986 | Buehler . | |
| 4,610,684 | 9/1986 | Knox et al. . | |
| 4,614,515 | 9/1986 | Tripp et al. . | |
| 4,645,073 | 2/1987 | Homan . | |
| 4,664,650 | 5/1987 | Urquhart et al. | 604/85 |
| 4,692,144 | 9/1987 | Carpenter . | |
| 4,715,851 | 12/1987 | Geisser et al. . | |
| 4,722,733 | 2/1988 | Howson . | |
| 4,731,053 | 3/1988 | Hoffman . | |
| 4,759,756 | 7/1988 | Forman et al. . | |
| 4,768,568 | 9/1988 | Fournier et al. . | |
| 4,781,679 | 11/1988 | Larkin . | |
| 4,784,658 | 11/1988 | Grabenkort . | |
| 4,804,366 | 2/1989 | Zdeb et al. . | |
| 4,820,269 | 4/1989 | Riddell . | |
| 4,834,149 | 5/1989 | Fournier et al. . | |
| 4,834,152 | 5/1989 | Howson et al. . | |
| 4,850,978 | 7/1989 | Dudar et al. . | |
| 4,863,454 | 9/1989 | LaBove . | |
| 4,871,354 | 10/1989 | Conn et al. . | |
| 4,871,360 | 10/1989 | Theeuwes . | |
| 4,874,344 | 10/1989 | Zdeb et al. | 604/56 |
| 4,874,366 | 10/1989 | Zdeb et al. . | |
| 4,906,103 | 3/1990 | Kao | 604/404 X |
| 4,978,337 | 12/1990 | Theeuwes | 604/85 |
| 4,997,430 | 3/1991 | Vander Heiden et al. | 604/414 |

SYSTEM FOR CREATING ON SITE, REMOTE FROM A STERILE ENVIRONMENT, PARENTERAL SOLUTIONS

BACKGROUND OF THE INVENTION

The disclosed invention was funded, at least in part, by NASA.

The present invention relates generally to the creation of solutions for intravenous administration. More specifically, the present invention relates to the creation on site, remote from sterile environments, of parenteral (intravenous) solutions.

Of course, it is common practice to administer many solutions, medicaments, agents, and the like to a patient intravenously (parenterally). These solutions are typically housed in containers, that are constructed from flexible plastic or glass. Typically, these parenteral solutions are housed in containers having volume capacities of at least one liter, referred to as large volume parenteral containers.

Large volume parenteral containers typically include solutions such as saline, dextrose, or lactated Ringer's. Although these solutions can be administered to a patient alone, typically agents or medicaments are added to the containers including the solution and the resultant product is then administered intravenously to the patient. To this end, the containers include additive or medication ports. Additionally, the containers include an access port for accessing the contents of the container.

In use, the parenteral container is suspended and an IV line or other access means is utilized to access the container through the access port. Typically, the IV line includes a spike that is designed to pierce a membrane in the port establishing fluid communication. A second end of the IV line is then directly inserted into the patient or coupled to a Y-site that provides fluid communication with the patient.

There are many situations wherein due to storage and/or weight limitations, or other concerns, it is not possible, or practical, to maintain an adequate inventory of parenteral solutions that may be necessary. For example, space shuttles, or the envisioned space stations, have severe restrictions on weight and storage capacities. Although it may be desirable to stock a number of intravenous solutions for use in an emergency, or for medical treatment, it is not possible due to space and storage limitations to inventory a large volume of such solutions in many situations. Likewise, in other situations, such as in a combat zone, it may not be possible to transport the necessary parenteral solutions.

Still further, even within health care facilities, storage and cost limitations may limit the inventory of product that is purchased and stored. Therefore, it may be desirable to compound on the premises the necessary parenteral solutions.

Although it is known in certain applications to compound and/or reconstitute drugs prior to use, typically such reconstitution processes are performed in sterile conditions, for example, under a laminar flow hood. Such sterile conditions would not typically be present in the aforementioned space station or combat zone. Likewise, current machinery for creating large volume parenteral products not only requires sterile conditions but also is quite bulky and heavy and not easily transportable.

Furthermore, typically reconstitution processes usually either require a prepackaged intravenous solution, i.e., a bag of saline or dextrose, or can only be utilized to make small volumes of solutions. These processes therefore are not conducive to the creation of large volume parenteral containers.

SUMMARY OF THE INVENTION

The present invention provides a system and method for creating on site, remote from a sterile environment, parenteral solutions in large volume parenteral containers for intravenous administration to a patient. For example, the present invention provides a system having a minimum weight and volume allowing the system to be transported in a space station, or other environment that is remote from sterile conditions, and used to create parenteral solutions in large volume parenteral containers that can be used for intravenous administration to a patient.

In an embodiment, this system comprises an empty large volume container including at least one port for accessing an interior of the container. The port includes a sterilizing filter for sterilizing a fluid fed through the port into the container. A second container is provided including a solute and having means for coupling the second container to the large volume container and thereby providing fluid communication therebetween allowing the solute to be received within the interior of the container. A sterile water source is also provided including means for placing the sterile water source in fluid communication with the port and allowing water to flow from the sterile water source into the interior of the container. This allows the solute, and sterile water that has been fed through the filter, to create a parenteral solution in the large volume parenteral container. The resultant parenteral solution, for example, saline, dextrose, or lactated ringer's, can then be administered to a patient.

In an embodiment, a system is provided for creating on site, remote from a sterile environment, parenteral solutions in a large volume parenteral container for intravenous administration to a patient comprising an empty large volume container. The container includes at least two ports for accessing an interior of the container. A first of the two ports includes a sterilizing filter for sterilizing a fluid fed through the port into the container. A device housing a solute is also provided that includes means that cooperates with a second of the two ports so that the device can be coupled to the container allowing fluid communication to be established between the interior of the container and the interior of the device. This allows the solute to be injected into the interior of the container. Also provided is a sterile water source including means for allowing the sterile water source to be coupled to the first port allowing fluid communication to be established between the sterile water source and the interior of the container.

In a preferred embodiment, the device includes a syringe body, that houses the solute, and a plunger that is used to force the solute out of the syringe body.

In another embodiment, a system for creating on site, remote from a sterile environment, parenteral solutions in a large volume parenteral container for intravenous administration to a patient is provided. The system includes an empty large volume parenteral container, including at least one port for accessing the interior of the container. The port includes a sterilizing filter for sterilizing a fluid fed through the port into the container. A second container is provided housing a solute in an interior thereof and having a first coupling member for coupling the second container to the port and establishing fluid communication between the interior of the second container and the interior of the large volume parenteral container. The second container includes at a second end thereof a second coupling member. Also provided is a sterile water source for providing sterile water. The sterile water source includes a coupling member for coupling the sterile water source to the second coupling member of the second container and establishing fluid communication between the sterile water source and the interior of the second container.

In an embodiment, the second container includes channels in an interior thereof.

In an embodiment, the second container defines a circular flow path within an interior thereof.

In an embodiment, the second container defines an elongated serpentine fluid flow path.

In an embodiment of the present invention, the solute is a powder.

In an embodiment of the present invention, the solute is a liquid.

In an embodiment of the present invention, the solute includes a component chosen from the group consisting of: dextrose, sodium chloride, and lactated Ringer's.

A method is also provided for preparing parenteral solutions on site, remote from a sterile environment. The method comprises the steps of: providing an empty large volume parenteral container including means for allowing the container to receive a solute and including a sterilizing filter; coupling a device including a solute to the container; causing the solute to enter an interior of the container; and feeding sterile water into the container so that it flows through the sterilizing filter.

In an embodiment of the method, the container includes two ports and the solute enters the interior of the container through one port and the sterile water enters the container through the second port.

In an embodiment of the method, the device comprises a second container that is coupled to a port and the sterile water source is coupled to a second end of the second container so that sterile water is fed into an interior of the second container and the solute and sterile water then flow through the port and the filter into the container.

In an embodiment of the method, the sterile water is fed into the container prior to the solute entering the container.

In an embodiment of the method, the sterile water enters the container contemporaneously with the solute.

In an embodiment of the method, the solute is a powder.

In an embodiment of the method, the solute is a liquid concentrate.

In an embodiment of the method, the solute includes a component chosen from the group consisting of: dextrose; sodium chloride; and lactated Ringer's.

In an embodiment of the method, a medicament is added to the resultant parenteral solution.

In an embodiment of the method, the parenteral solution is administered intravenously to a patient.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and method for formulating a predetermined amount of sterile solution for intravenous administration into a patient. The invention allows the transportation and storage of the necessary components to create a number of varied parenteral solutions that heretofore were not possible due to storage, weight, and space limitations.

For example, in an environment such as a space station, space vehicle, or combat zone, the present invention allows the transportation and storage of the necessary components to create, as needed, parenteral solutions for use. Furthermore, the present invention provides a method and process wherein sterile solutions, that can be administered to a patient, can be created and mixed in a non-sterile environment without special equipment. Further, a relatively large number of parenteral solutions can be formulated using a relatively small number of bags and the like.

In all of the embodiments of the present invention, empty large volume parenteral containers can be transported and then used to create containers housing parenteral solutions. For example, such end products as lactated Ringer's, saline, half-normal saline, and 5% dextrose can be created. Further, these solutions can then be used with agents and medicaments that are typically added to the solution to allow the infusion into a patient of products that heretofore were not possible in certain environments remote from sterile conditions.

Figure 1:
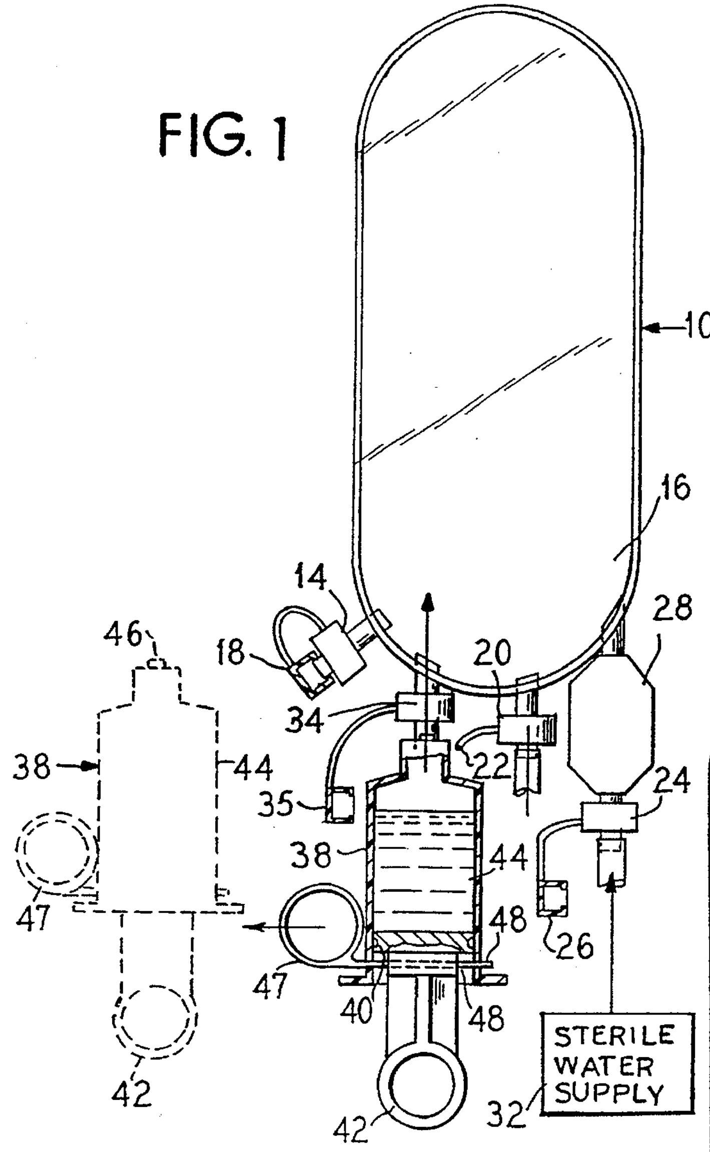
FIG. 1 illustrates a cross-sectional perspective view of an embodiment of the system for creating on site, remote from a sterile environment, parenteral solutions in a large volume parenteral container.

Referring now to FIG. 1, the system of the present invention includes an empty large volume parenteral container 10. The parenteral container 10 can be any size large volume parenteral container. For example, containers housing one liter of solution can be used. The container 10 includes a body 12 constructed from a flexible plastic material such as polyvinyl chloride, ethylene vinyl acetate, polyolefins, or combinations thereof.

As illustrated, preferably, the container 10 includes a plurality of ports. Of course, the container 10 can include any number of ports and although four ports are illustrated, a greater or lesser number of ports can be provided.

The first port 14 is a medicament or additive port that allows an agent or medicament to be injected into the interior 16 of the container 10. Although any type of port arrangement can be utilized, preferably, the first port 14 includes a one way valve. An example of which is a one way valve manufactured by Burron Medical Corporation. The use of a one way valve allows a needleless, or blunt cannula to be used to inject a medicament into the interior 16 of the container 10. Additionally, a bidirectional valve available from Burton Medical Corporation can be used. Of course, if desired, the port can include a typical pierceable membrane and the port can be accessed by a pointed cannula needle. Additionally, a preslit resealable membrane and blunt cannula structure can be used. Such a preslit membrane and cannula is disclosed in U.S. patent application Ser. No. 07/147,414, "Preslit Injection Site and Associated Cannula", abandoned in favor of U.S. patent application Ser. No. 07/539,278, the disclosures of which are incorporated herein by reference. The advantage of either needleless cannula system is with respect to the improvements in safety and ease of use relative to prior practice.

The illustrated embodiment also includes a port protector 18. The port protector 18 ensures sterility of an interior of the port 14 until it is desired to access the container 10 through the port 14. Preferably, to limit trash generation, the port protector 18 is tethered to the first port 14.

A second port 20, that functions as an access port, is provided that allows solution to flow out of the container 10. The second port 20 can comprise a standard port that is accessed by a spike that is typically used on an IV administration set. Preferably, a bidirectional valve is provided within the port 20 to allow fluid communication between the interior 16 of the container 10 and an IV administration set. Likewise, in the preferred embodiment illustrated, a port protector 22 that is tethered to the port 20 is provided.

A third port 24 is provided that also includes a port protector 26 tethered to the port. However, this port is coupled to a microbial or sterilizing filter 28 that is sealed onto one end of the large volume parenteral container 10 and at the other end to the third port 24. The sterilizing filter 28 provides a fluid path therethrough and terminates at an opening 30 in fluid communication with an interior 16 of the container 10. Accordingly, any fluid that flows through the third port 24 must flow through the sterilizing filter 28. The sterilizing filter 28 is utilized to sterilize the fluid that flows through the third port 24 into the container 10. For example, a 0.22 micron sterilizing filter 28 can be utilized.

Again, preferably, a bidirectional valve is utilized in the third port 24 to allow fluid flow into the interior 16 of the container 10. As discussed in more detail hereinafter, the third port 24 and sterilizing filter 28 allow for water to flow into the interior 16 of the container 10 creating the parenteral solution in the parenteral container.

Although the third port 24 is described as a separate element with respect to the sterilizing filter 28, it should be appreciated that the third port 24 can be an integral part of the filter.

In an embodiment, the sterilizing filter 28 is removably secured to the container 10. To this end, a luer connection or the like can be used to removably secure the filter to the container. This allows the sterilizing filter 28 to be removed after the parenteral solution has been created in the container. To accomplish this, a bidirectional valve can be located between the container and the filter so that when the filter is removed, fluid does not flow out of the container.

The advantage of this structure, in part, is with respect to long term storage of the resultant parenteral solution containing containers. If stored for a long period of time, there is a potential for growth through the filter that could potentially contaminate the solution in the containers.

The third port 24 is designed so that it can be coupled to a sterile water source 32. The sterile water source 32 is designed so that it can pump sterile water into the interior 16 of the container 10. The sterile water source 32 can be any apparatus that creates sterile water that can be fed into the container. For example, the sterile water source 32 can be the Sterile Water for Injection System (SWIS) developed by the Sterimatics Division of Millipore Corporation for NASA. Such a system includes a particulate filter, activated charcoal filter, cation bed, anion bed, and microbial filter.

The container 10 includes a fourth port 34. The fourth port 34 also allows a material to be injected into an interior 16 of the container 10. However, as discussed hereinafter, the fourth port 34 is specifically designed to receive the solute. Again, preferably the fourth port 34 includes a one way valve to allow the solute to enter the interior 16 of the container 10, but prevents the contents in the interior of the container from flowing out of the container through the fourth port 34. Likewise, the fourth port 34 includes a port protector 35.

As illustrated in FIG. 1, the system also includes a prefilled syringe 38. The prefilled syringe 38 includes the solute 40. Within the container 10, the solute 40 is mixed with the sterile water from the sterile water source 32 and creates a parenteral solution such as dextrose, saline, and lactated Ringer's.

The solute, as previously stated, when combined with sterile water, or other fluid creates a parenteral solution. As used herein, a solute refers to a composition that when combined with water, or other fluid, creates a parenteral solution. For example, the solute can be sodium chloride, dextrose, or lactated Ringer's. The solute can either be in a liquid concentrated form or in a powder form. Due to sterilization concerns, the liquid concentrated form is probably preferred.

Even in the case of dextrose powders, it has been found that the dissolution rates of the powder are such that containers of parenteral solution can be created on an expedited basis. For example, assuming that the sterile water source 32 can produce no more than six liters of sterile water per hour, the fill time of a one liter parenteral container would be ten minutes. Ten minutes is sufficient time to dissolve the necessary dextrose powder allowing a 5% dextrose solution to be created that can then be administered intravenously.

The sterile water source 32 can include a metering device (not shown) to ensure that only one liter of water is injected into the container 10, if a one liter solution is to be created. Of course, the metering device can also, if desired, be coupled to the container 10. Additionally, a clamshell (not shown) or other structure can be used that circumscribes the flexible container 10. The clamshell can be designed to only allow the container 10 to accept a predetermined amount of fluid.

As illustrated, the prefilled syringe 38 includes a plunger 42 designed to move in a piston motion within an interior of the body 44 of the syringe 42. Of course, by moving the plunger 42 toward the end of the body 44 of the syringe, the solute within the syringe body is expelled. Preferably, the syringe 38 terminates in a blunt end 46. The blunt end 46 of the syringe 36 can either include a cap or other protective covering that is removed prior to use.

In the preferred embodiment illustrated, a pin 47 is provided that is received within apertures 48 in the syringe body 44 and plunger 42 preventing inadvertent movement of the plunger and thereby an inadvertent discharge of the solute from the syringe.

The syringe 38 is designed to dock with the fourth port 34. Because the fourth port 34 includes a one-way valve, this establishes fluid communication and the solute can be injected through the fourth port 34, and specifically, through the one way valve, into the interior 16 of the container 10. Once the solute is injected into the container 10, the syringe

38 can be removed because the one way valve prevents the solute and the parenteral solution from exiting the port.

When the solute has been so injected into the container 10 it can mix with the sterile water that is injected into the container from the sterile water source. This allows parenteral solutions to be created as necessary in an expedient manner.

Figure 2:
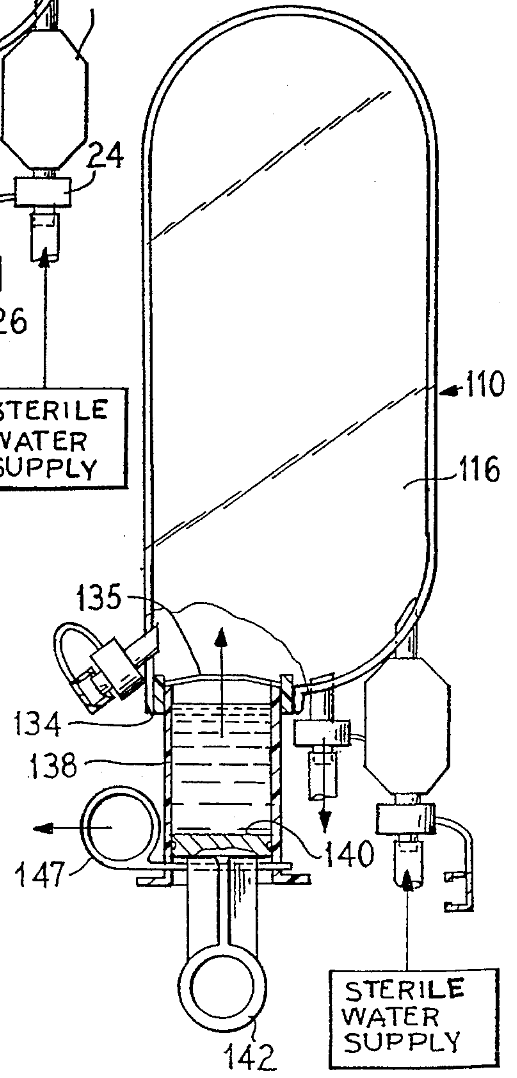
FIG. 2 illustrates a cross-sectional perspective view of another embodiment of the system of the present invention.

Referring now to FIG. 2, an embodiment of the system is illustrated. The structure is substantially similar to the structure set forth in FIG. 1 except that the prefilled syringe 138 is designed to dock with the container 110 by being received within a depressed port 134 in the container 110. The depressed port 134 includes a frangible seal member 135. Additionally, the depressed port 134 includes means for locking the syringe 138 to the port, and therefore the container 110.

Accordingly, once the syringe 138 docks with the depressed port 134 and the pin 147 is removed, the plunger 142 can be pushed downwardly causing a seal on the syringe to rupture as well as the seal 135 on the container 110. This allows the solute 140 to be injected into the interior 116 of the container 110. Because the syringe 138 and depressed port 134 are designed so that once the syringe docks with the container it remains securely fastened thereto, the syringe 138 remains attached to the container 110 during the creation of the parenteral solution and use of the product, i.e., infusion of the solution into a patient.

Figure 3:
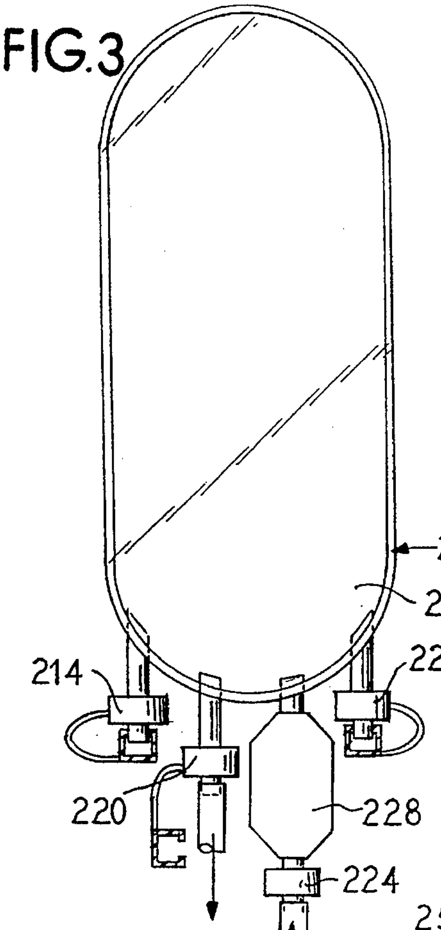
FIG. 3 illustrates a cross-sectional view of another embodiment of the system of the present invention.
Figure 3:
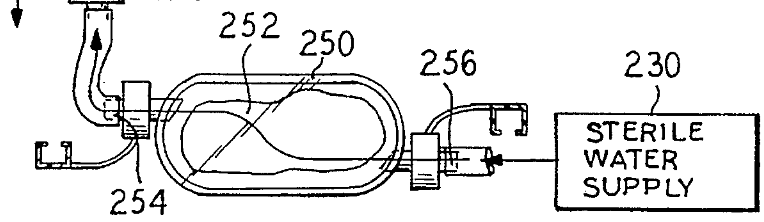

Referring now to FIG. 3, a further embodiment of the present invention is illustrated. Again, a large volume empty parenteral container 210 is provided. As in the previous embodiments, the solute and sterile water are added to the container to create a parenteral solution. To this end, in the illustrated embodiment, a plurality of ports are provided.

Again, a medicament port 214, for adding a medicament, is provided. Additionally, an administration port 220 from which solution can be administered to the patient is provided. In the illustrated embodiment, a redundant or extra port 223 is provided. Of course, this port 223 is not necessary but functions to provide additional means for accessing the container.

Similar to the previous embodiments, a third port 224 is provided having a sterilizing filter 228 that is connected at one end to the large volume parenteral container 210 and at the other end to the port 224. Again, a fluid path is defined from the port 224, through the filter 228, and into the interior 216 of the container 210.

In this embodiment of the system, a second container 250 is provided. The second container 250 houses the solute 252. Again, the solute can be a liquid concentrate or a powder for creating a parenteral solution, e.g., saline, dextrose, or lactated Ringer's.

The second container 250 includes a first coupling member 254 and a second coupling member 256. The first coupling member 254 is designed to couple with the third port 224 of the large volume container 210 providing fluid communication between the interior 216 of the second container 250 and the third port 224. Thus, fluid flow is established between the interior of the second container and the filter 228 and interior 216 of the container 210.

The second coupling member 256 of the second container 250 is designed to couple with a sterile water source 230. The second coupler 256 allows fluid to flow from the sterile water source 230 through the second container 250 wherein it can mix with the liquid concentrate or powder contained therein. The resultant mixture then flows through the sterilizing filter 228. As the resultant fluid flows through the filter 228, it is filtered. It has been found that even if a powder is used, a 0.22 micron filter will not become clogged if properly wetted. From the filter 228, the solution flows into the container 210 wherein the solution can create a parenteral solution in a large volume parenteral container.

In each of the first and second coupling members, one way valves are provided. This allows fluid to flow in only one direction, toward the interior 216 of the container 210.

Figure 4:
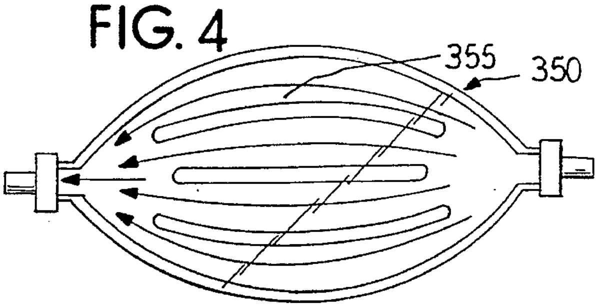
FIG. 4 illustrates a cross-sectional perspective view of an embodiment of the device of the system of FIG. 3.

Referring to FIG. 4, an embodiment of the second container 350 is illustrated. As illustrated, channels 355 are provided within the container to ensure that the sterile water flow flushes the solute out of the bag. The channels 355 create fluid flow paths (illustrated by arrows) that are designed to insure that there is a mixing and flow of the solute out of the second container into the large volume parenteral container. The channels 355 can be created in a number of ways, for example, by ridge members sealed within an interior 316 of the container or sealing portions of the body of the container to each other.

Figure 5:
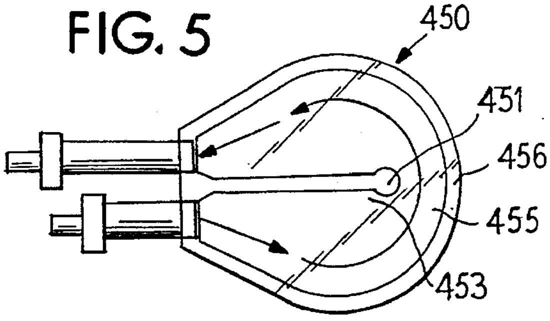
FIG. 5 illustrates a cross-sectional view of a further embodiment of the device of the system of FIG. 3.

Referring to FIG. 5, a further embodiment of the second container 450 is illustrated wherein a circular flow path (illustrated by an arrow) is provided. The container includes a divider 451 at the center 453 of its interior 455 to define a flow path. Fluid is accelerated at the top 456 of the arc through constriction and aids in the mixing.

Figure 6:
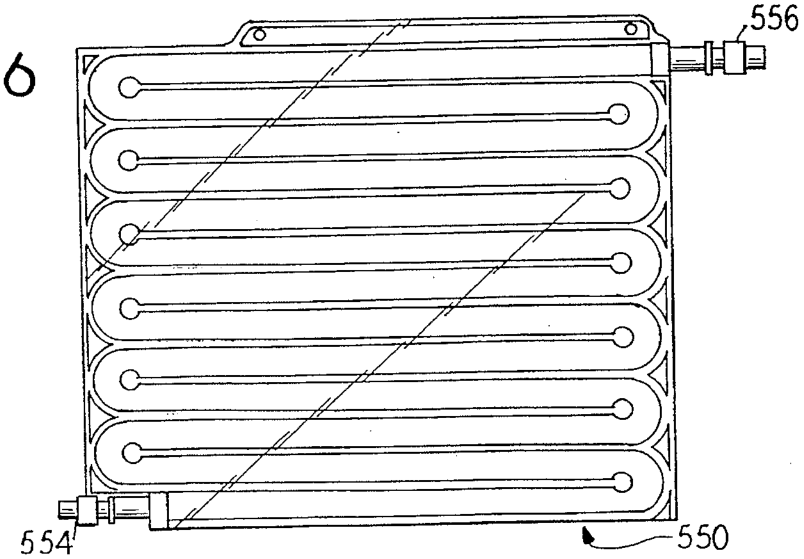
FIG. 6 illustrates a cross-sectional view of another embodiment of the device of the system of FIG. 3.

Referring now to FIG. 6, a further, preferred, embodiment of the second container 550 is illustrated. In the embodiment illustrated, a serpentine flow path is provided. The second container 550 effectively consists of a long, narrow serpentine path that forces complete mixing of the solute and sterile water within the second container 550. This ensures complete mixing of the solute and sterile water. The length of the fluid path (i.e., number of times the serpentine path reverses itself) assists in insuring complete mixing. Again, first and second coupling members 554 and 556 are provided.

By way of example and not limitation, examples of the present invention will now be given.

Examples of the system of the present invention are as follows. These examples allow for the creation of lactated Ringer's, normal saline, half-normal saline, and 5% dextrose.

| Embodiment | Approximate Volume (Solute) ml | Approximate Weight (Solute) grams | Approximate Volume (Package) ml | Approximate Weight (Filled Package) grams |
|---|---|---|---|---|
| Powder in second container | | | | |
| Lactated Ringer's | — | — | — | — |
| Normal Saline | 6.47 | 9.00 | 109.96 | 43.80 |

-continued

| Embodiment | Approximate Volume (Solute) ml | Approximate Weight (Solute) grams | Approximate Volume (Package) ml | Approximate Weight (Filled Package) grams |
|---|---|---|---|---|
| Half-Normal Saline | 3.24 | 4.50 | 106.72 | 39.30 |
| 5% Dextrose | 45.00 | 45.50 | 159.94 | 84.80 |
| Concentrate in second container | | | | |
| Lactated Ringer's | 40.00 | 47.7 | 218.00 | 106.00 |
| Normal Saline | 50.00 | 58.10 | 218.00 | 106.00 |
| Half-Normal Saline | 25.00 | 29.05 | 218.80 | 102.80 |
| 5% Dextrose | 71.40 | 91.60 | 147.00 | 147.00 |
| Powder in syringe | | | | |
| Lactated Ringer's | — | — | — | — |
| Normal Saline | 6.47 | 9.00 | 31.46 | 16.90 |
| Half-Normal Saline | 3.24 | 4.50 | 28.22 | 12.40 |
| 5% Dextrose | 45.00 | 45.50 | 188.29 | 89.20 |
| Concentrate in syringe | | | | |
| Lactated Ringer's | 40.00 | 47.7 | 188.29 | 95.00 |
| Normal Saline | 50.00 | 58.10 | 188.29 | 97.30 |
| Half-Normal Saline | 25.00 | 29.05 | 163.29 | 68.25 |
| 5% Dextrose | 71.40 | 91.60 | 301.19 | 144.64 |

The measured densities and weights of concentrates at target fill volumes used in the above examples are as follows:

| Formulation | Density at 25° C. (g/cc) | Proposed Solution Volume (mL) | Weight (g) |
|---|---|---|---|
| 9 g/50 mL Sodium Chloride | 1.162 | 50 | 58.1 |
| 70% Dextrose | 1.283 | 71.4 | 91.6 |
| Lactated Ringer's Concentrate B* | 1.193 | 40 | 47.7 |
| Lactated Ringer's Concentrate C* | 1.153 | 50 | 57.6 |

*5.94 gm sodium chloride, 0.297 potassium chloride, 0.198 mg calcium chloride dihydrate, 3.07 gm sodium lactate.

The present invention provides the ability to create, as needed, a substantial supply of parenteral solutions using initial supplies that have a limited weight and volume.

For example, based on the above, the following volumes and weights are only needed to afford one the ability to create 120 one liter parenteral containers, exclusive of the sterile water source.

Total one liter solutions that can be created 120—30 dextrose, 30 sodium chloride, 30 50% sodium chloride, and 30 lactated Ringer's:

| Embodiment Utilizing Syringe - Powder | | | |
|---|---|---|---|
| Weight Calculations | | | |
| Target Bags | 71.7 Grams/Unit | 8600 Grams | 57.32% |
| 5% Dextrose | 89.2 Grams/Unit | 2676 Grams | 17.83% |
| Normal Saline | 16.9 Grams/Unit | 507 Grams | 3.38% |
| Half-Normal Saline | 12.4 Grams/Unit | 372 Grams | 2.48% |
| Lactated Ringer's | 95.0 Grams/Unit | 2850 Grams | 18.99% |
| | Total Weight | 15005 Grams | 100.00% |
| Volume | | | |

-continued

| Embodiment Utilizing Syringe - Powder | | | |
|---|---|---|---|
| Calculations | | | |
| Target Bags | 235.0 mL | 28200.00 mL | 68.38% |
| 5% Dextrose | 188.3 mL | 5648.70 mL | 13.68% |
| Normal Saline | 31.5 mL | 943.80 mL | 2.28% |
| Half-Normal Saline | 28.2 mL | 846.00 mL | 2.06% |
| Lactated Ringer's | 188.3 mL | 5648.70 mL | 13.68% |
| | Total Volume | 41287.20 mL | 100.00% |

Alternatively, if a liquid concentrate is used in the syringe embodiment.

| Embodiment Utilizing Syringe - Liquid Concentrate | | | |
|---|---|---|---|
| Weight Calculations | | | |
| Target Bags | 65.0 Grams/Unit | 7800 Grams | 39.09% |
| 5% Dextrose | 144.6 Grams/Unit | 4339 Grams | 21.74% |
| Normal Saline | 97.3 Grams/Unit | 2919 Grams | 14.63% |
| Half-Normal Saline | 68.3 Grams/Unit | 2048 Grams | 10.26% |
| Lactated Ringer's | 95.0 Grams/Unit | 2850 Grams | 14.28% |
| | Total Weight | 19956 Grams | 100.00% |
| Volume Calculations | | | |
| Target Bags | 229.7 mL | 27560.40 mL | 51.47% |
| 5% Dextrose | 301.2 mL | 9035.70 mL | 16.88% |
| Normal Saline | 188.3 mL | 5648.70 mL | 10.55% |
| Half-Normal Saline | 188.3 mL | 5648.70 mL | 10.55% |
| Lactated Ringer's | 188.3 mL | 5648.70 mL | 10.55% |
| | Total Volume | 53542.20 mL | 100.00% |

If the embodiment utilizing the second container is used:

| Embodiment Utilizing Second Container - Powder | | | |
|---|---|---|---|
| Weight Calculations | | | |
| Target Bags | 65.0 Grams/Unit | 7800 Grams | 48.70% |
| 5% Dextrose | 84.8 Grams/Unit | 2544 Grams | 15.88% |
| Normal Saline | 43.8 Grams/Unit | 1314 Grams | 8.20% |
| Half-Normal Saline | 39.3 Grams/Unit | 1179 Grams | 7.36% |
| Lactated Ringer's | 106.0 Grams/Unit | 3180 Grams | 19.85% |
| | Total Weight | 16017 Grams | 100.00% |
| Volume Calculations | | | |
| Target Bags | 229.7 mL | 27560.40 mL | 60.71% |
| 5% Dextrose | 159.9 mL | 4798.20 mL | 10.57% |
| Normal Saline | 110.0 mL | 3298.80 mL | 7.27% |
| Half-Normal Saline | 106.7 mL | 3201.60 mL | 7.05% |
| Lactated Ringer's | 218.0 mL | 6540.00 mL | 14.41% |
| | Total Volume | 45399.00 mL | 100.00% |

Alternatively, if the liquid concentrate is used with the second container embodiment:

| Embodiment Utilizing Second Container - Concentrate | | | |
|---|---|---|---|
| Weight Calculations | | | |
| Target Bags | 65.0 Grams/Unit | 7800 Grams | 37.36% |
| 5% Dextrose | 147.0 Grams/Unit | 4410 Grams | 21.12% |
| Normal Saline | 106.0 Grams/Unit | 3180 Grams | 15.23% |
| Half-Normal Saline | 77.0 Grams/Unit | 2309 Grams | 11.06% |
| Lactated Ringer's | 106.0 Grams/Unit | 3180 Grams | 15.23% |
| | Total Weight | 20879 Grams | 100.00% |
| Volume Calculations | | | |
| Target Bags | 229.7 mL | 27560.40 mL | 50.74% |
| 5% Dextrose | 263.0 mL | 7890.00 mL | 14.52% |
| Normal Saline | 218.0 mL | 6540.00 mL | 12.04% |
| Half-Normal Saline | 193.0 mL | 5790.00 mL | 10.66% |
| Lactated Ringer's | 218.0 mL | 6540.00 mL | 12.04% |
| | Total Volume | 54320.40 mL | 100.00% |

By way of further illustration, the data below illustrates the ability to create 120 one liter solutions each of dextrose, sodium chloride, 50% sodium chloride, or lactated Ringer's:

| Embodiment Using Second Container - Powder | | | |
|---|---|---|---|
| Weight Calculations | | | |
| Target Bags | 65.0 Grams/Unit | 7800 Grams | 19.18% |
| 5% Dextrose | 84.8 Grams/Unit | 10176 Grams | 25.02% |
| Normal Saline | 43.8 Grams/Unit | 5256 Grams | 12.92% |
| Half-Normal Saline | 39.3 Grams/Unit | 4716 Grams | 11.60% |
| Lactated Ringer's | 106.0 Grams/Unit | 12720 Grams | 31.28% |
| | Total Weight | 40668 Grams | 100.00% |
| Volume Calculations | | | |
| Target Bags | 229.7 mL | 27560.40 mL | 27.86% |
| 5% Dextrose | 159.9 mL | 19192.80 mL | 19.40% |
| Normal Saline | 110.0 mL | 13195.20 mL | 13.34% |
| Half-Normal Saline | 106.7 mL | 12806.40 mL | 12.95% |
| Lactated Ringer's | 218.0 mL | 26160.00 mL | 26.45% |
| | Total Volume | 98914.80 mL | 100.00% |

Alternatively, if a liquid concentrate is used:

| Embodiment Using Second Container - Concentrate | | | |
|---|---|---|---|
| Weight Calculations | | | |
| Target Bags | 65.0 Grams/Unit | 7800 Grams | 12.98% |
| 5% Dextrose | 147.0 Grams/Unit | 17640 Grams | 29.34% |
| Normal Saline | 106.0 Grams/Unit | 12720 Grams | 21.16% |
| Half-Normal Saline | 77.0 Grams/Unit | 9234 Grams | 15.36% |
| Lactated Ringer's | 106.0 Grams/Unit | 12720 Grams | 21.16% |
| | Total Weight | 60114 Grams | 100.00 |
| Volume Calculations | | | |
| Target Bags | 229.7 mL | 27560.40 mL | 20.48% |
| 5% Dextrose | 263.0 mL | 31560.00 mL | 23.45% |
| Normal Saline | 218.0 mL | 26160.00 mL | 19.44% |
| Half-Normal Saline | 193.0 mL | 23160.00 mL | 17.21% |
| Lactated Ringer's | 218.0 mL | 26160.00 mL | 19.44% |
| | Total Volume | 134600.40 mL | 100.00% |

If the syringe embodiment is used:

| Embodiments Using Syringe - Powder | | | |
|---|---|---|---|
| Weight Calculations | | | |
| Target Bags | 71.7 Grams/Unit | 8600 Grams | 25.13% |
| 5% Dextrose | 89.2 Grams/Unit | 10704 Grams | 31.28% |
| Normal Saline | 16.9 Grams/Unit | 2028 Grams | 5.93% |
| Half-Normal Saline | 12.4 Grams/Unit | 1488 Grams | 4.35% |
| Lactated Ringer's | 95.0 Grams/Unit | 11400 Grams | 33.31% |
| | Total Weight | 34220 Grams | 100.00% |
| Volume Calculations | | | |
| Target Bags | 235.0 mL | 28200.00 mL | 34.84% |
| 5% Dextrose | 188.3 mL | 22594.80 mL | 27.92% |
| Normal Saline | 31.5 mL | 3775.20 mL | 4.66% |
| Half-Normal | 31.5 mL | 3775.20 mL | 4.66% |

-continued

| Embodiments Using Syringe - Powder | | | |
|---|---|---|---|
| Saline | | | |
| Lactated Ringer's | 188.3 mL | 22594.80 mL | 27.92% |
| | Total Volume | 80940.00 mL | 100.00% |

Alternatively, if a liquid concentrate is used:

| Embodiment Using Syringe - Liquid Concentrate | | | |
|---|---|---|---|
| Weight Calculations | | | |
| Target Bags | | | |
| 5% Dextrose | 65.0 Grams/Unit | 7800 Grams | 13.82% |
| Normal Saline | 144.6 Grams/Unit | 17357 Grams | 30.76% |
| Half-Normal Saline | 97.3 Grams/Unit | 11676 Grams | 20.69% |
| Lactated Ringer's | 68.3 Grams/Unit | 8190 Grams | 14.52% |
| | 95.0 Grams/Unit | 11400 Grams | 20.20% |
| | Total Weight | 56423 Grams | 100.00% |
| Volume Calculations | | | |
| Target Bags | 229.7 mL | 27560.40 mL | 20.96% |
| 5% Dextrose | 301.2 mL | 36142.80 mL | 27.49% |
| Normal Saline | 188.3 mL | 22594.80 mL | 17.18% |
| Half-Normal Saline | 188.3 mL | 22594.80 mL | 17.18% |
| Lactated Ringer's | 188.3 mL | 22594.80 mL | 17.18% |
| | Total Volume | 131487.60 mL | 100.00% |

Examples of methods of the present invention are as follows:

POWDER IN FLOW-THROUGH SECOND CONTAINER

1. Remove container from foil pouch (preferably the containers are stored in foil pouches).
2. Remove second container from foil pouch.
3. Remove port protector from inlet port on filter of container.
4. Remove port protector from the port of second container.
5. Connect port of second container to inlet on port on filter.
6. Connect outlet of sterile water source to remaining port on second container.
7. Initiate flow of water from sterile water source into second container and then into the container. Filling will take approximately 10 minutes.
8. Allow container to fill.
9. If desired, a medicament can be added by connecting a prefilled syringe containing prescribed medication and injecting medication to the medication port into the container.
10. After the container is filled, disconnect the second container from the sterile water source.
11. Disconnect the container from second container.
12. Connect outlet port of container to inlet of administration set.
13. Purge set and connect set to patient.
14. Begin flow of IV solution to patient.

LIQUID CONCENTRATE IN FLOW-THROUGH SECOND CONTAINER

1. Remove container from foil pouch.
2. Remove second container from foil pouch.
3. Remove port protector from inlet port on filter of container.
4. Remove port protector from port of second container.
5. Connect port of second container to inlet on container filter.
6. Connect outlet of sterile water source to remaining port on second container.
7. Initiate flow of water through sterile water source. Filling will take approximately 10 minutes.
8. Allow container to fill.
9. Again, if desired, medication can be added to the solution and container.
10. After container is filled, disconnect second container from sterile water source.
11. Disconnect second container from container.
12. Remove port protector from outlet port of container.
13. Connect outlet port of container to inlet of administration set.
14. Purge set and connect set to patient.
15. Begin flow of IV solution to patient.

POWDER IN SYRINGE

1. Remove container from foil pouch.
2. Remove port protector from inlet port on filter.
3. Connect outlet of sterile water source to inlet port on filter.
4. Initiate flow of water through sterile water source into the container. Filling will take approximately 10 minutes.
5. Allow container to fill.
6. Remove port protectors from syringe docking site and from syringe containing proper solute.
7. Snap end of syringe into docking site. Syringe will lock into place.
8. Connect plunger handle to plunger of syringe.
9. Remove retaining pin from barrel of syringe.
10. Depress plunger of syringe, injecting solute into container.
11. If desired, a medicament can be added. To this end, a prefilled syringe containing prescribed medication is connected to the medication port.
12. Inject medication into the container.
13. After container is filled, disconnect container from sterile water source.
14. Remove port protector from inlet of administration set.
15. Connect outlet port of LVP to inlet of administration set.

16. Purge set and connect set to patient.

17. Begin flow of IV solution to patient.

CONCENTRATE IN SYRINGE

1. Remove container from foil pouch.
2. Remove port protector from inlet port on filter.
3. Connect outlet of sterile water source to inlet port on filter.
4. Initiate flow of water through sterile water source. Filling will take approximately 10 minutes.
5. Allow container to fill.
6. Remove port protectors from container injection site and from syringe containing proper solute.
7. Connect syringe to injection site.
8. Connect plunger handle to plunger of syringe.
9. Remove retaining pin from barrel of syringe.
10. Depress plunger of syringe, injecting solute into bag.
11. Disconnect syringe from injection site.
12. Again, if desired, a medicament can be added.
13. After the container is filled, disconnect the container from the sterile water source.
14. Remove port protector from inlet of administration set.
15. Connect outlet port of container to inlet of administration set.
16. Purge set and connect set to patient.
17. Begin flow of IV solution to patient.

Initial sterilization of the system, i.e., after the individual components are created, but before the resultant parenteral solution is created, can be accomplished in a variety of ways. For the liquid concentrate embodiments sterilization can be accomplished using conventional techniques. To this end, the container 10 and second container or prefilled syringe solute can be terminally sterilized.

If powders are used, sterilization is more difficult but it may be possible to terminally sterilize the container or syringe containing the powder through gamma irradiation. However, it is possible to manufacture the powder under sterile conditions and then fill the second container or prefilled syringe with powder under sterile conditions.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A system for creating on site, remote from a sterile environment, parenteral solutions in a large volume parenteral container for intravenous administration to a patient comprising:

an empty large volume containers including at least one port for accessing an interior of the container and having a sterilizing filter for sterilizing a fluid fed through the port into the container;

a second container including a solute and having means for coupling the second container to the large volume container and providing fluid communication therebetween allowing the solute to be received within the interior of the container; and a sterile water source including means for placing the sterile water source in fluid communication with the port and allowing sterile water to flow from the sterile water source into the interior of the container.

2. The system of claim 1 wherein the solute is in a powder form.

3. The system of claim 1 wherein the solute is in a liquid concentrate form.

4. The system of claim 1 wherein the solute is chosen from the group consisting of: dextrose; sodium chloride; and lactated Ringer's.

5. The system of claim 1 wherein a parenteral solution created is chosen from the group consisting of saline, dextrose, and lactated Ringer's.

6. The system of claim 1 wherein the second container includes a syringe prefilled with solute.

7. The system of claim 1 wherein the second container is so constructed and arranged as to allow sterile water to flow through an interior thereof into the interior of the large volume container.

8. The system of claim 1 wherein the large volume container includes an additive port and an administration port.

9. The system of claim 1 wherein the sterilizing filter is removably secured to the large volume container.

10. A system for creating on site, remote from a sterile environment, parenteral solutions in a large volume parenteral container for intravenous administration to a patient comprising:

an empty large volume container including at least two ports for accessing an interior of the container, a first of the two ports including a sterilizing filter for sterilizing a fluid fed through the port into the container;

a device housing a solute and including means that cooperate with a second of the two ports to allow the device to be coupled onto the container and fluid communication to be established between the interior of the container and an interior of the device allowing the solute to be injected into the interior of the container; and a sterile water source including means for allowing the sterile water source to be coupled to the first port and fluid communication to be established between the fluid source and an interior of the container.

11. The system of claim 10 wherein the solute is in a powder form.

12. The system of claim 10 wherein the solute is in a liquid concentrate form.

13. The system of claim 10 wherein the solute includes a component chosen from the group consisting of: dextrose; sodium chloride; and lactated Ringer's.

14. The system of claim 10 wherein the device is a syringe.

15. The system of claim 14 wherein the syringe includes a blunt end.

16. The system of claim 14 wherein the syringe includes means for preventing an inadvertent discharge of the contents of the syringe.

17. The system of claim 16 wherein the means includes a removable pin that is received within at least one aperture of a body of the syringe and one aperture in a plunger of the syringe.

18. The system of claim 14 wherein the second port includes means for locking the syringe to the container.

19. The system of claim 10 wherein the container includes an additive port and an administration port.

20. The system of claim 14 wherein the second port includes means for releasably receiving an end of the syringe.

21. The system of claim 10 wherein the second port includes a frangible seal that is so constructed and arranged that it ruptures to allow solute to be injected into the container.

22. The system of claim 10 wherein the second port includes a one way valve.

23. The system of claim 10 wherein the first port includes a bidirectional valve.

24. The system of claim 10 wherein the sterilizing filter is removably secured to the container.

25. A system for creating on site, remote from a sterile environment, parenteral solutions in a large volume, parenteral container for intravenous administration to a patient comprising:

an empty large volume parenteral container having a plurality of ports including at least one port for accessing an interior of the container, the port including a sterilizing filter for sterilizing a fluid fed through the port into the container;

a second container housing a solute in an interior thereof and having a first coupling member for coupling the second container to the port and establishing fluid communication between the interior of the second container and the interior of the large volume parenteral container and a second coupling member; and a sterile water source for providing sterile water and including a coupling member for coupling the sterile water source to the second coupling member of the second container and establishing fluid communication from the sterile water source and the interior of the second container.

26. The system of claim 25 wherein the solute is in a powder form.

27. The system of claim 25 wherein the solute is in a liquid concentrate form.

28. The system of claim 25 wherein the solute includes a component chosen from the group consisting of: dextrose; sodium chloride; and lactated Ringer's.

29. The system of claim 25 wherein the second container includes in an interior thereof channels.

30. The system of claim 25 wherein the second container includes an interior that defines a circular fluid flow path.

31. The system of claim 25 wherein the second container includes an interior that defines an elongated serpentine fluid flow path.

32. The system of claim 25 wherein the large volume parenteral container includes an additive port and an administration port.

33. The system of claim 25 wherein the port includes a one way valve.

34. The system of claim 25 wherein the port includes a bidirectional valve.

35. The system of claim 25 wherein the sterilizing filter is removably secured to the large volume parenteral container.

36. A method for preparing parenteral solutions on site, remote from a sterile environment, comprising the steps of:

providing an empty large volume parenteral container including means for allowing the container to receive a solute and including a sterilizing filter;

coupling a device including a solute to the container;

causing the solute to enter an interior of the container;

feeding sterile water into the container so that it flows through the sterilizing filter before entering the container; and allowing the solute and sterile water to mix and create a parenteral solution.

37. The method of claim 36 comprising the steps of:

providing the container with two ports; and causing the solute to enter the interior of the container through one port and the sterile water to enter the container through a second port.

38. The method of claim 36 wherein the sterile water is fed into the second container prior to the solute entering the second container.

39. The method of claim 36 wherein the sterile water enters the second container contemporaneously with the solute.

40. The method of claim 36 wherein the solute is a powder.

41. The method of claim 36 wherein the solute is a liquid concentrate.

42. The method of claim 36 wherein the solute includes a component chosen from the group consisting of dextrose; sodium chloride; and lactated Ringer's.

43. The method of claim 36 including the step of adding a medicament to the parenteral solution.

44. The method of claim 36 wherein the parenteral solution is administered intravenously to the patient.

45. The method of claim 36 wherein the parenteral solution created is chosen from the group consisting of dextrose, saline, and lactated Ringer's.

46. The method of claim 36 including the step of removing the sterilizing filter from the large volume parenteral container after the parenteral solution is created.

47. A method for preparing parenteral solutions on site, remote from a sterile environment, comprising the steps of:

providing an empty large volume parenteral container including means for allowing the container to receive a solute and including a sterilizing filter;

coupling a device including a solute to the container;

causing the solute to enter an interior of the container;

feeding sterile water into the container so that it flows through the sterilizing filter;

allowing the solute and sterile water to mix and create a parenteral solution; and providing for the device a second container that is coupled to a port and the sterile water source is coupled to an end of the second container so that sterile water is fed into the interior of the second container and the solute and sterile water then flows through the port and the filter into the container.

* * * * *